United States Patent

Gulsby

[11] Patent Number: 4,464,190
[45] Date of Patent: Aug. 7, 1984

[54] HYDROCARBON GAS PROCESS
[75] Inventor: Jerry G. Gulsby, Kingwood, Tex.
[73] Assignee: Gulsby Engineering, Inc., Tex.
[21] Appl. No.: 409,314
[22] Filed: Aug. 18, 1982
[51] Int. Cl.³ .............................................. F25J 3/02
[52] U.S. Cl. .......................................... 62/24; 62/38
[58] Field of Search ................... 62/38, 39, 23, 24, 27, 62/28

[56]      References Cited
      U.S. PATENT DOCUMENTS
   4,203,742  5/1980  Agnihotri ............................... 62/38

Primary Examiner—Frank Sever
Attorney, Agent, or Firm—Ranseler O. Wyatt

[57] ABSTRACT

The processing of gaseous streams of feed gas containing hydrocarbons, and other gases of similar volatility, to recover components such as ethane, propane and heavier hydrocarbons from a residue gas containing methane, by cooling the incoming raw gas and to separate the desired products by distillation. The cooling action is obtained by expanding the raw feed gas from a high feed pressure to a lower pressure at which distillation occurs. In the present invention, the raw feed gas is divided into two gas streams before expansion, the first stream, which consists primarily of vapor, is again cooled through a heat exchange device, and is then expanded through an expansion valve to lower the pressure and then fed into the top of the conventional demethanizer column. The second stream, is selectively divided into two streams, one of which passes through a controlled expansion valve and back into the feed conduit, and the other passes through an expander-compressor into the feed conduit, where the combined gases pass into a separator which discharges the vapors into a discharge line and discharges a liquid into another feed conduit, which again divides the stream into two streams, directing one stream into the demethanizing column at a midway point, and the other stream passed through a heat exchanger to raise the temperature of the stream and then discharging same into the demethanizing column beneath the midway inlet. The demethanizing column is operated at 410 psia, with a top temperature of −136° F. for recovery of ethane and rejection of propane and a top temperature of −109° F. for rejection of ethane. In the recovery process, approximately 77.2% ethane is recovered when in the recovery mode, and 88% propane is retained when in the rejection mode.

5 Claims, 1 Drawing Figure

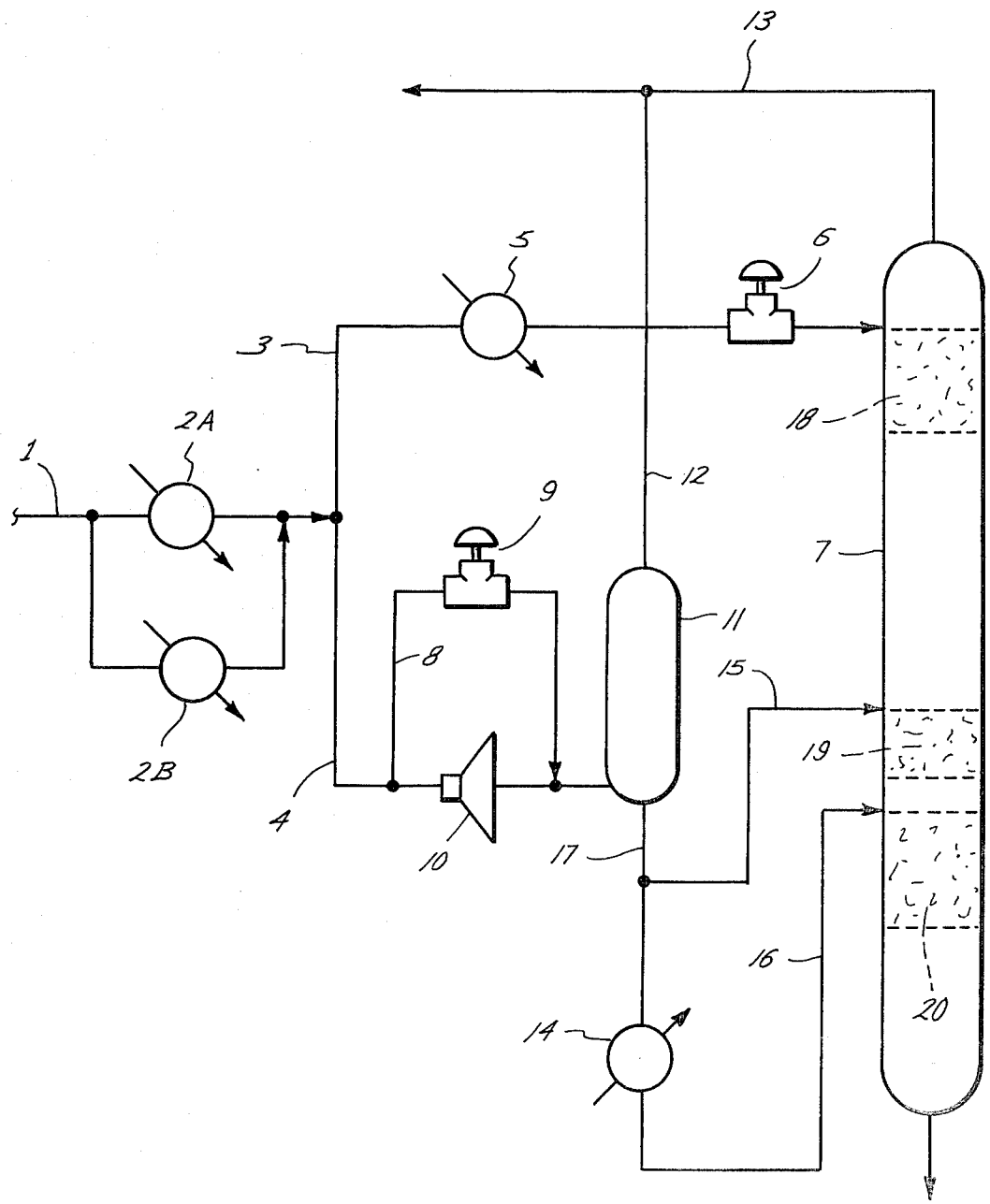

HYDROCARBON GAS PROCESS

SUMMARY OF THE INVENTION

A process for recovery of desired components of a gaseous feed stream wherein the feed stream is divided, cooled, then separated into two streams, the first being primarily vapors, which are cooled and expanded to lower the pressure and temperature, and directed into a demethanizing column as residue gas, and reflex, and the other stream, primarily vapors, is selectively divided, one stream passing through controlled expansion means and back into the feed line and the other stream passing through an expander, and the combined stream passing into a separator, wherein the vapors pass into a discharge conduit, and the liquid passes into another conduit, where the liquid stream is again divided, one stream passing into the demethanizer at the midway point, and the other stream passing through a heat exchanger, raising the temperature of the gaseous stream and delivering same into the demethanizer beneath the midway point, maintaining a demethanizer column pressure of approximately 410 psia, and a top temperature of $-136°$ F. for recovery of approximately 72.2% ethane, and $-109°$ F. for rejection of ethane, retaining approximately 88% propane.

BRIEF DESCRIPTION OF THE DRAWING

The FIGURE discloses a diagrammatic flow sketch of the process employed.

DESCRIPTION OF THE PREFERRED EMBODIMENT

Incoming feed gas in conduit 1 passes through heat exchangers 2A and 2B, and the conduit 1 is divided into the first conduit 3 and the second conduit 4, with identical vapors passing into the first conduit 3 and into the second conduit 4. The feed gas in conduit 3, which comprises substantially 15% of the total inlet feed gas, passes through another heat exchanger 5, which lowers the temperature of the feed gas before passing the gas through controlled expansion valve 6 which lowers the pressure, and thence into the top of the demethanizer column 7. The demethanizer column is maintained with a pressure of 410 psia and the top temperature for recovery of ethane is $-136°$ F.; and for the rejection of ethane, to retain propane, the temperature is maintained at $-109°$ F.

The second stream of incoming feed gas is approximately 85% of the inlet gas, and passes through conduit 4 into a dividing point, where part of the stream of feed gas is selectively diverted through conduit 8, and the controlled expansion valve 9, for control of the reduction of pressure and temperature, but primarily the other part passes through the expander 10, where the pressure and temperature are reduced, and the two streams selectively combined and pass into the divider 11, where the vapors induced by the expansion pass into the conduit 12, and into the residue gas discharge line 13, leading from the top of the demethanizer column 7. The liquid passes into the conduit 17 and the resultings stream is again divided, one portion passing through the heat exchanger 14, where the temperature of the liquid is raised before sending it into the demethanizer column 7, through the conduit 16. The other portion of the liquid by-passes the last mentioned heat exchanger and flows into the demethanizer column 7 at a midway point, through conduit 15; the line 16 extends from the heat exchanger 14 and terminates in the demethanizer column below the midway point. This arrangement puts a liquid/vapor stream into the demethanizer column at the top of the first packed bed 18, and liquid from the cooled feed gas onto the second packed bed 19, midway of the demethanizer column, and liquid from the feed gas of a raised temperature onto the bottom packed bed 20 in the demethanizer column.

What I claim is:

1. In a process for the recovery of components of volatile gas containing methane and heavier components by processing said gas through a demethanizer column, the improvement comprising: eliminating the requirement of pumps in said process by, introducing a stream of feed gas under pressure into a heat exchange unit to lower the temperature of said gas stream, dividing the stream into two streams, the first of said two streams being primarily vapors, which are again cooled by passing same through a heat exchanger, and then through a controlled expansion valve and into the top of the demethanizer column, directing said second stream through an expansion means, lowering the pressure and temperature and then through a divider, separating the vapors and liquid, discharging the vapors into a discharge conduit, and dividing the liquid into two streams, one of which is fed into the demethanizer column at the midway point, and the other stream passing through a heat exchanger unit to raise the temperature of the fluid and then feeding same into the demethanizer column at a feed point beneath the midway feed point.

2. The process taught in claim 1 wherein the pressure maintained in the demethanizer column is approximately 410 psia.

3. The process taught in claim 1 wherein the temperature within the demethanizer column is maintained within the range of $-136°$ F. and 79° F.

4. The process taught in claim 1 wherein to recover ethane, the top temperature of the demethanizer column is maintained at approximately $-136°$ F.

5. The process taught in claim 1 wherein to reject ethane and retain propane, a top temperature of $-109°$ F. is maintained in the demethanizer column.

* * * * *